United States Patent [19]
McPhee

[11] Patent Number: 5,558,650
[45] Date of Patent: Sep. 24, 1996

[54] ELASTOMERIC SYRINGE ACTUATION DEVICE

[75] Inventor: Charles J. McPhee, Huntington Beach, Calif.

[73] Assignee: I-Flow Corporation, Irvine, Calif.

[21] Appl. No.: 300,157

[22] Filed: Sep. 2, 1994

Related U.S. Application Data

[63] Continuation-in-part of Ser. No. 208,729, Mar. 9, 1994, Pat. No. 5,429,607.
[51] Int. Cl.$^6$ .................................................. A61M 5/315
[52] U.S. Cl. .......................... 604/218; 604/131; 604/207; 433/89
[58] Field of Search ........................... 604/218, 131–135, 604/187, 207, 208, 209, 210; 128/DIG. 12; 433/80, 89, 90

[56] References Cited

U.S. PATENT DOCUMENTS

| | | | |
|---|---|---|---|
| 4,381,006 | 4/1983 | Genese . | |
| 4,597,754 | 7/1986 | Thill et al. | 604/154 |
| 4,636,197 | 1/1987 | Chu | 604/131 |
| 4,755,172 | 7/1988 | Baldwin | 604/131 |
| 4,950,163 | 8/1990 | Zimble | 433/215 |
| 4,950,265 | 8/1990 | Taylor | 606/1 |
| 4,966,585 | 10/1990 | Gangemi | 604/131 |
| 5,024,662 | 6/1991 | Menes et al. | 604/131 |
| 5,041,094 | 8/1991 | Perego et al. | 604/143 |
| 5,078,679 | 1/1992 | Reese | 604/121 |
| 5,100,389 | 3/1992 | Vaillancourt | 604/135 |

FOREIGN PATENT DOCUMENTS

| | | |
|---|---|---|
| 69428 | 9/1968 | German Dem. Rep. . |
| 220582A1 | 1/1984 | German Dem. Rep. . |

*Primary Examiner*—Randall L. Green
*Assistant Examiner*—V. Alexander
*Attorney, Agent, or Firm*—Klein & Szekeres

[57] ABSTRACT

A syringe actuation device comprises an elastomeric element that is removably attachable to the outlet tip of a syringe, and to a grip member that allows the elastomeric element to be pulled along the syringe barrel, so as to seat against the distal end of the syringe plunger. In first and second embodiments, the elastomeric element is attached between a grommet, that fits around the outlet tip, and an end cap, having a finger grip, that engages the distal end of the plunger. When the grommet is seated around the outlet tip, and the end cap is engaged against the distal end of the plunger with the plunger in its withdrawn position, the elastomeric element is stretched along the syringe, thereby biasing the plunger toward its inserted position. As the elastomeric element restores itself to its unstretched configuration, it pushes the plunger into the syringe barrel. In the first embodiment, the elastomeric element is an elastic strap having first and second ends removably secured to the grommet so as to be length-adjustable, and an intermediate portion secured to the end cap. In the second embodiment, the elastomeric element is a continuous elastic band removably secured to both the grommet and the end cap. In a third embodiment, the elastomeric element has a hole that receives the outlet tip, and the grip member is removably engageable with the elastomeric element for pulling the elastomeric element so as to seat against the distal end of the plunger.

22 Claims, 7 Drawing Sheets

_fig.24_

_fig.25_

_fig.27_

_fig.26_

_fig.28_

_fig.29_

ELASTOMERIC SYRINGE ACTUATION DEVICE

CROSS-REFERENCE TO RELATED APPLICATION

This application is a continuation-in-part of application Ser. No. 08/208,729; filed Mar. 9, 1994; now U.S. Pat No. 5,429,607.

BACKGROUND OF THE INVENTION

This invention relates generally to the field of fluid infusion devices for medical applications. More specifically, it relates to infusion devices used for the administration of a liquid medicament to a patient from a filled syringe into an intravenous (IV) administration system.

Various devices have been developed for the intravenous (IV) infusion of liquid medicaments into a patient at a controlled flow rate over an extended period of time. For example, gravity flow IV administration sets have been employed for many years, and more recently, IV administration sets with electrically powered pumps have been developed.

There are applications in which a more compact and inexpensive type of infusion device is desired or required. For example, in addition to direct infusion from a syringe, it is frequently necessary to infuse a secondary fluid into a primary IV flow from a gravity flow or electrically-pumped IV administration set. Also, infusion into an ambulatory patient frequently requires an infusion device that is less bulky, less complex, and easier to use than gravity flow or pump-powered devices. For such applications, relatively complex self-powered infusion devices are frequently used.

With a typical, manually actuated IV administration syringe, infusion over an extended period of time is usually impractical or inconvenient, and achieving a substantially constant flow rate throughout the infusion is often difficult. To overcome these problems, the prior art has devised a variety of mechanisms for actuating the syringe so as to achieve a more or less constant fluid flow over an extended period of time. One type of syringe actuation mechanism is that which utilizes either internal or external springs to displace the plunger of the syringe. Examples of such mechanisms are shown in the following U.S. Pat. No. : 4,381,006—Genese; 4,597,754—Thill et al.; 4,608,042—Vanderveen et al.; 4,623,330—Laby et al.; 4,755,172—Baldwin; 4,966,585—Gangemi; 5,078,679—Reese; and 5,100,389—Vaillancourt.

While the spring-powered mechanisms of the prior art over-come, to varying degrees, the above-mentioned problems associated with manual syringes, they suffer from other shortcomings, such as complexity, relatively heavy weight, and relatively high costs. Those with spring mechanisms inside the syringe necessitate increased costs in the manufacture of the syringe itself, making such mechanisms inappropriate for single use, disposable syringes. Those employing a spring mechanism external to the syringe are typically cumbersome to use, often necessitating the extra step of installing the syringe in a dispenser.

Another approach has been to use elastomeric bands to provide the plunger-depressing force in a syringe. Examples of such devices are shown in U.S. Pat. No. 4,636,197—Chu; U.S. Pat. No. 4,950,163—Zimble; U.S. Pat. No. 5,024,662—Menes et al.; and German Democratic Republic (GDR) Patent No. 69,428. The elastomerically powered syringes are typically simpler and less costly to manufacture than the spring actuated devices discussed above. They are also usually easier and more convenient to use, and they are more readily adaptable for single use applications. A principal drawback to these prior art elastomerically powered devices, however, is that they require specially designed syringes, and they are thus not readily adapted for use with standard IV administration syringes.

Therefore, there has been an unfulfilled need for a compact, self-actuated IV administration device that provides a nearly constant flow rate over an extended period of time, while also being economical to manufacture, easy and convenient to use, and adaptable for single use applications with the standard IV administration syringe.

SUMMARY OF THE INVENTION

Broadly, the present invention is an elastomeric syringe actuation device, comprising an elastomeric element, in the form of a strap or band, having a proximal portion that fits over the outlet tip of an IV administration syringe, and a distal portion that is engageable against the distal end of the plunger of the syringe. In several preferred embodiments, the device comprises a grommet assembly that fits over the outlet tip of the syringe; an end cap, having a handle or finger grip, that engages the distal end of the plunger of the syringe; and an elastomeric element that connects the grommet assembly and the end cap, so that when the grommet assembly is seated around the outlet tip, and the end cap is seated on the distal end of the plunger, the elastomeric element extends longitudinally along diametrically opposite sides of the syringe, between the grommet assembly and the end cap. When the device is installed on a previously-filled syringe having its plunger pulled out of the syringe barrel to its withdrawn position, the elastomeric element is stretched, placing it under tension, so that it biases the plunger toward its inserted position. As the elastomeric element restores itself to its unstretched configuration, it provides a driving force against the plunger to push the plunger into the barrel of the syringe, thereby expressing the fluid contained in the barrel out of the outlet tip.

In one specific preferred embodiment, the elastomeric element is an elongate elastic strap, having a single hole near one end, and a plurality of holes in a linear array near the other end. The grommet assembly comprises an externally-threaded, hollow, cylindrical, bolt-like attachment fitting that fits through the single hole in the one end of the strap, and, with the strap ends overlapping, through one of the plurality of holes near the other end. An internally-threaded annular collar is removably threaded onto the end of the fitting that extends through the strap ends to removably lock the ends of the strap to the grommet assembly. Optionally, the grommet assembly may define an orifice or internal passage with a diameter large enough to accommodate a typical closure cap for an IV line.

The end cap comprises a short, hollow, cylindrical sleeve with a closed distal end wall that includes an annular peripheral flange. The hollow interior of the sleeve is dimensioned to receive the circular thumb rest of the plunger, and the interior wall surface of the sleeve is provided with latch means for releasably grasping the thumb rest. Extending distally from the exterior surface of the distal end wall of the end cap is a ring-shaped handle or finger grip, having a large central orifice. Two diametrically opposed slots are provided in the annular flange to accommodate the elastic strap.

The strap extends longitudinally from the grommet assembly to the end cap, passing through one slot in the end cap flange, from the proximal side of the flange to the distal side thereof. The strap then extends laterally across the exterior surface of the distal end wall of the end cap, through the orifice of the finger grip, to the other slot, through which it passes back to the proximal side of the flange. From there, the strap extends longitudinally back to the grommet assembly.

The device is used by installing it on a filled infusion syringe having its plunger in the withdrawn position, and having outflow from its outlet tip obstructed by any suitable, conventional closure of the outlet tip, or by a conventional clamp applied to a catheter or conduit attached to the outlet tip. The grommet assembly is attached to the strap by inserting the externally-threaded fitting through the single hole in the one end of the strap, and through a selected one of the plurality of holes in the other end, the selection being based on the size of the syringe on which the device is to be installed. The strap is locked to the grommet assembly by threading the annular, internally-threaded collar onto the fitting. The grommet assembly is then seated around the outlet tip of the syringe, and the strap is stretched until the thumb rest of the plunger is received in the end cap of the device, thereby placing the strap under tension and biasing the plunger toward its inserted position in the syringe barrel. With outflow from the syringe being obstructed, however, inward movement of the plunger from its withdrawn position to its inserted position is prevented.

When it is desired to discharge the contents of the syringe, the outflow obstruction means are removed. The potential energy represented by the elastomeric tension in the strap is then released, generating a linearly-directed driving force against the thumb rest to drive the plunger into the barrel, thereby expressing the contents of the syringe out of the outlet tip. This driving force has a very slow rate of decay over time, so that the flow rate expressed from the syringe remains reasonably close to its nominal level until the syringe is nearly empty.

In another preferred embodiment, the elastomeric element comprises a continuous elastic band, with a pair of diametrically-opposed holes. Instead of a two-piece grommet assembly, a unitary grommet is placed around the outlet tip and inserted into a first one of the holes in the band. The grommet may advantageously have an orifice that is large enough to accommodate a typical IV line closure cap. The end cap comprises an arcuate grip portion extending distally from the distal end wall, a pair of diametrically-opposed band guides extending radially outwardly from the end wall, and a knob or button extending distally from the distal end of the grip portion. The band is passed through the band guides and around the exterior surface of the grip portion, with the knob or button being received in the second one of the holes in the band.

Still another embodiment comprises a continuous elastic band with a single hole; a tapered fitting that removably fits over the outlet tip of the syringe; and a removable band-pulling implement (in place of the end cap). The fitting is placed on the outlet tip, and is then inserted through the hole in the band. The band-pulling implement is then attached to the band to pull it over the distal end of the plunger, after which the implement is removed. The fitting is removed to expose the outlet tip just prior to use, thereby maintaining the sterility of the tip.

A number of variations may be applied to one or more of the embodiments described above. In one variation of the second embodiment, for example, the second band hole and the button or knob are omitted. In another variation, most applicable to the first and second embodiments, the end cap has a flattened distal end wall surface defined between a pair of parallel, distally-extending band guides. A similar variation that is most applicable to the third embodiment employs a distal plunger surface having a pair of parallel, distally-extending band guides. In still another variation, applicable to any of the embodiments, a combination end cap/band puller is removable from the elastic strap or band, so that the end cap can be reused, even if the elastic strap or band is discarded.

A further variation, most applicable to the second and third embodiments, employs a pair of relatively thin or narrow elastic bands, rather than a single, relatively thick or wide band, to reduce the effort of installing the device on a syringe. A similar advantage is obtained by using an elastic member that comprises a bifurcated strap, joined at its ends, each of which is apertured. In use, the ends are overlapped so that a grommet assembly can be inserted through both apertures. The bifurcated main portion of the strap, now formed into a loop, is pulled over the distal plunger end (or the distal surface of the end cap) when the syringe is ready for use.

From the foregoing, it can be seen that the present invention provides an elastomerically-powered IV administration syringe actuation device that is easy to use, and adaptable for use with standard IV administration syringes in a wide variety of sizes. Moreover, the present invention is simple and inexpensive to manufacture, and thus is readily adaptable to single use (disposable) applications. These and other advantages of the present invention will be more readily understood from the detailed description that follows.

DETAILED DESCRIPTION OF THE PREFERRED EMBODIMENTS

Referring to the drawings, an elastomeric syringe actuation device 10, in accordance with a first preferred embodiment of the present invention, is shown both installed on (FIGS. 1 and 4) and separate from (FIGS. 2, 3, and 5 through 7) a standard IV administration syringe 12. The syringe 12 has an outlet tip 14 at its proximal end, of the standard configuration that accommodates a typical Luer fitting (not shown). Extending distally from the tip 14 is a substantially cylindrical barrel 16, the interior of which provides a reservoir for a liquid therapeutic agent (hereinafter referred to as a "medicament"). plunger 18 is received within the barrel 16 for longitudinal movement between a withdrawn position (shown in FIGS. 1 and 4) and an inserted position. The plunger 18 has an actuation portion 19 extending distally from the barrel 16, the actuation portion 19 terminating in a flattened, substantially circular thumb rest 20.

The elastomeric syringe actuation device 10 comprises a grommet assembly 22 that fits over and seats around the outlet tip 14 of the syringe 12; an end cap 24 that engages the thumb rest 20 of the syringe plunger 18; and an elastomeric element 26 that connects the grommet assembly 22 and the end cap 24.

Figure 5:
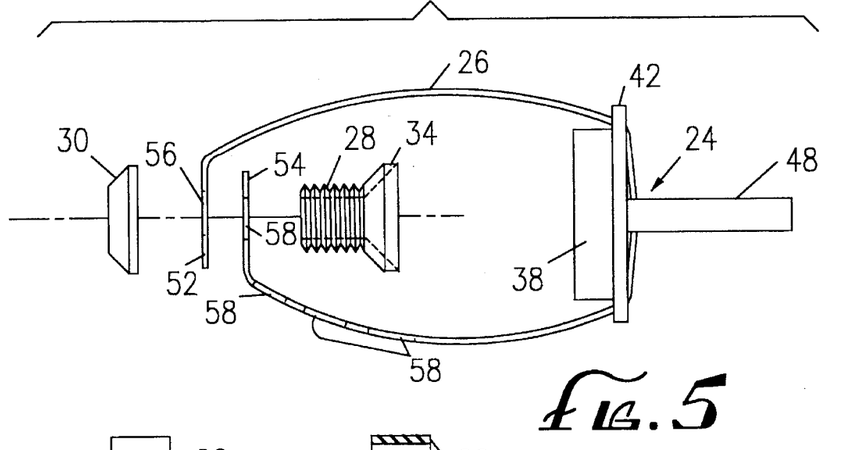
FIG. 5 is an exploded elevational view of the syringe actuation device, in accordance with the first preferred embodiment of the present invention.
Figure 6:
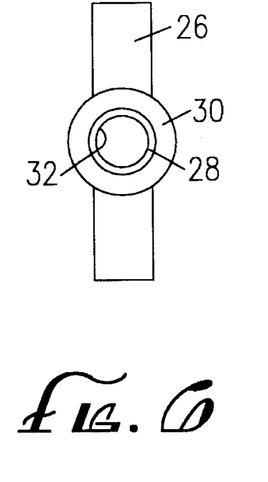
FIG. 6 is an elevational view, taken along line 6—6 of FIG. 3.
Figure 7:
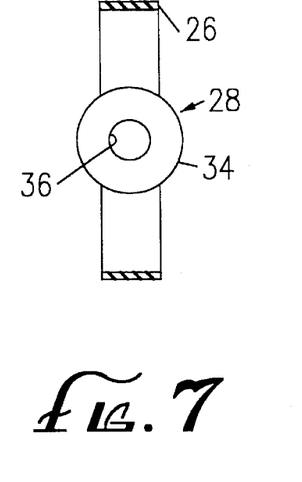
FIG. 7 is a cross-sectional view, taken along line 7—7 of FIG. 3.

As best shown in FIGS. 5 through 7, the grommet assembly 22 comprises an externally-threaded, cylindrical, bolt-like fitting 28 and an internally-threaded annular collar 30 that is removably threaded onto the fitting 28. The fitting 28 has an axial bore 32 and an enlarged-diameter head 34 having a central orifice 36 that communicates with the bore 32.

Figure 4:
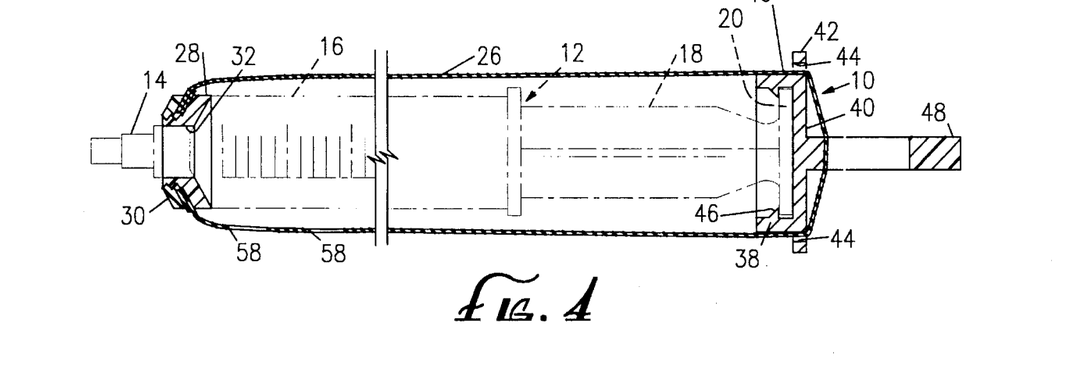
FIG. 4 is a cross-sectional view, taken along line 4—4 of FIG. 3, showing the first preferred embodiment of the syringe actuation device installed in its stretched position on a syringe.

As best shown in FIG. 4, the end cap 24 comprises a short, cylindrical sleeve 38 having an open proximal end, and a closed distal end wall 40 that includes an annular peripheral flange 42. The hollow interior of the sleeve 38 is dimensioned to receive the thumb rest 20, which seats against the interior surface of the end wall 40. The flange 42 is provided with a pair of diametrically-opposed guide slots 44. Extending radially inwardly from the interior wall surface of the sleeve 38 are a pair of diametrically-opposed fingers 46 that provide means for releasably engaging or latching the thumb rest 20. Extending distally from the exterior surface of the distal end wall 40 of the end cap 24 is a ring-shaped handle or finger grip 48, having a large central orifice 50.

In the first preferred embodiment, as best shown in FIG. 5, the elastomeric element 26 is an elongate elastic strap having a first end portion 52 and a second end portion 54, with an intermediate portion therebetween. A single hole 56 is formed in the strap 26 near the first end portion 52 and a plurality of holes 58 are formed in a linear array near the second end portion 54. The end cap 24 is attached to the approximate middle of the length of the strap 26 by passing one of the end portions 52, 54 through one of the slots 44 in the end cap flange 42, from the proximal side to the distal side thereof. That one end portion is then extended across the exterior (distal) surface of the distal end wall 40, through the orifice 50 of the finger grip 48, and then through the other slot 44 back to the proximal side of the flange 42. The one end portion of the strap is then pulled through the slots 44 until the end cap 24 is situated approximately mid-way along the length of the strap 26.

The strap end portions 52, 54 are removably attached to the grommet assembly 22 by means of the single hole 56 and a selected one of the plurality of holes 58. Specifically, as best shown in FIG. 5, with the annular collar 30 removed from the fitting 28 the proximal end of the fitting 28 is passed through the single hole 56, and, with the strap end portions 52, 54 overlapping, through one of the plurality of holes 58, selected on the basis of the size of the syringe on which the device 10 is to be installed. The collar 30 is then threaded onto the fitting 28 until the strap end portions 52, 54 are snugly captured between the collar 30 and the head 34 of the fitting 28.

Figure 1:
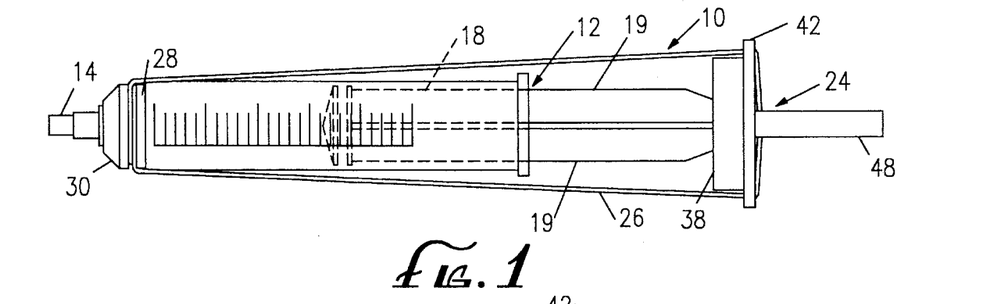
FIG. 1 is a side elevational view of a syringe actuation device, in accordance with a first preferred embodiment of the present invention, showing the device installed on a standard IV administration syringe.
Figure 2:
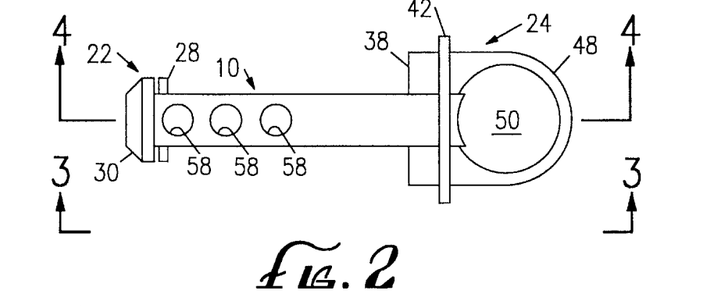
FIG. 2 is a side elevational view of the first preferred embodiment of the syringe actuation device of FIG. 1, the device having been removed from the syringe and rotated 90 degrees around the longitudinal axis of FIG. 1.
Figure 3:
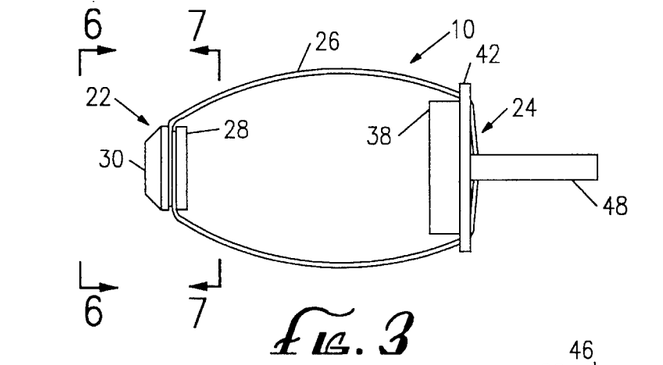
FIG. 3 is an elevational view of the first preferred embodiment of the syringe actuation device, taken along line 3—3 of FIG. 2.

Because the slots 44, through which the strap 26 is passed, are disposed radially outwardly from the syringe barrel 16 by their placement in the flange 42, the slots 44 and the flange 42 provide an "outrigger" effect, whereby the strap 26 is positioned away from the syringe barrel 16, as best shown in FIG. 1. This separation between the strap 26 and the syringe barrel 16 prevents abrasion of the strap 26 against the syringe barrel 16, thereby preventing damage to the strap 26, and allowing for a smoother movement of the syringe plunger 18 when the device 10 is used in the manner described below.

To use the actuation device 10, a syringe 12 is filled with the desired quantity of medicament, and then the outflow from the syringe is obstructed by conventional means, such as a clamp (not shown) on the IV tubing (not shown) connected to the outlet tip 14 of the syringe. With the outflow obstructed, the plunger 18 remains in its withdrawn position, as shown in FIGS. 1 and 4.

The actuation device 10 is then installed on the syringe 12 by seating the grommet assembly 22 around the outlet tip 14, with the tip 14 extending through the central orifice 36 and axial bore 32 of the fitting 28. The end cap 24 is then pulled distally, by means of the finger grip 48, until the thumb rest 20 of the plunger 18 can be seated within the sleeve 38, with the edge of the thumb rest 20 being engaged by the latching fingers 46. In this position, shown in FIGS. 1 and 4, the elastomeric element or strap 26 is stretched so that it is under tension, thereby biasing the plunger 18 toward its inserted position.

When the obstruction to the syringe outflow is removed (e.g., by removing the above-mentioned clamp), the plunger 18 is free to be moved toward its inserted position. This is accomplished by the release of the potential energy stored in the stretched strap 26 as it elastomerically restores itself to its unstretched configuration, thereby generating a linearly-directed force against the thumb rest 20 which drives the plunger 18 in the proximal direction toward its inserted position. The proximal movement of the plunger 18 into the barrel 16 causes the medicament therein to be discharged from the outlet tip 14. The driving force generated by the strap 26 has a very slow rate of decay, so that the flow rate of medicament from the syringe 12 remains reasonably close to a preselected nominal flow rate until the syringe 12 is empty, or nearly so.

A syringe 12 may be filled and stored with the actuation device 10 installed on it as described above (and with the syringe's outflow suitably obstructed). Should the strap 26 break while the syringe 12 is stored (or while it is being used), one or both of the latching fingers 46 in the end cap sleeve 38 is likely to be retained in engagement with the thumb rest 20, thereby keeping the actuation device 10 from "flying" off of the syringe 12 in response to the release of energy when the strap 26 breaks. In addition, the end cap 24 and the grommet assembly 22 are securely (although removably) attached to the strap 26, so that, even if the strap 26 should break, all of the components of the device 10 are held together, with a minimal probability of separation or loss of a component.

Figures 8, 10:
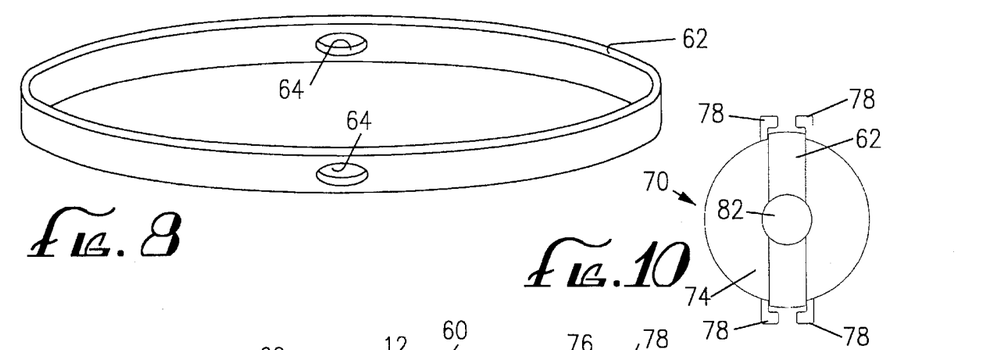
FIG. 8 is a perspective view of an elastic band configured for use in a second preferred embodiment of the invention.
FIG. 10 is an elevational view, taken along line 10—10 of FIG. 9.
Figure 9:
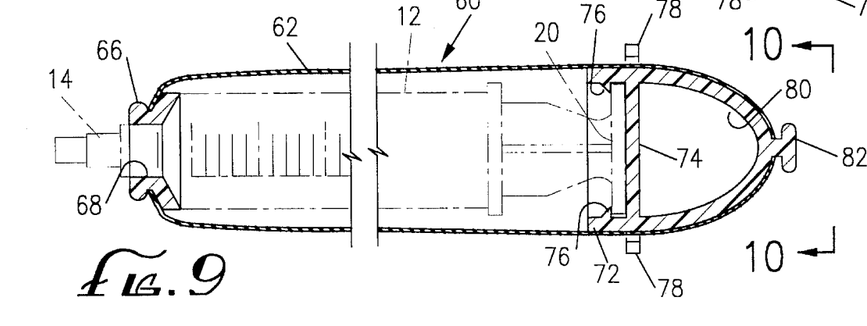
FIG. 9 is a cross-sectional view, similar to that of FIG. 4, showing the second preferred embodiment of the invention installed on a syringe.

A syringe actuation device 60, in accordance with a second preferred embodiment of the invention, is shown in FIGS. 8, 9, and 10. In this second embodiment, the elastomeric element is a continuous elastic band 62, having a pair of diametrically-opposed holes 64. A unitary grommet 66, having a hollow bore 68, is inserted in a first one of the holes 64 to attach the band 62 to the grommet 66. The outlet tip 14 of the syringe 12 is inserted into and through the bore 68, so that the grommet 66 is seated around the outlet tip 14.

An end cap 70 comprises a short cylindrical sleeve 72 having an open proximal end, and a closed distal end wall 74. The hollow interior of the sleeve 72 is dimensioned to receive the thumb rest 20 of the syringe 12, which seats against the interior surface of the end wall 74. Extending radially inwardly from the interior wall surface of the sleeve 72 are a pair of diametrically-opposed fingers 76 that provide means for releasably engaging or latching the thumb rest 20.

The end cap 70 is provided with a pair of diametrically-opposed band guides, each of which comprises a pair of guide fingers 78 extending radially outwardly from the end wall 74, and then angled toward each other substantially at a right angle, with a gap therebetween into which the band 62 can be inserted. The guide fingers 78 position the elastic band 62 so that it is spaced from the syringe barrel, and thus function much like the end cap slots 44 of the first embodiment.

An arcuate grip portion 80 extends distally from the distal end wall 74, and a knob or button 82 extends distally from the distal end of the grip portion 80. The band 62 is passed between the band guide fingers 78 and around the exterior surface of the grip portion 80, with the knob or button 82 being received in the second one of the holes 64 in the band 62 to secure the band 62 to the grip portion 80 of the end cap 70.

Figures 11, 13:
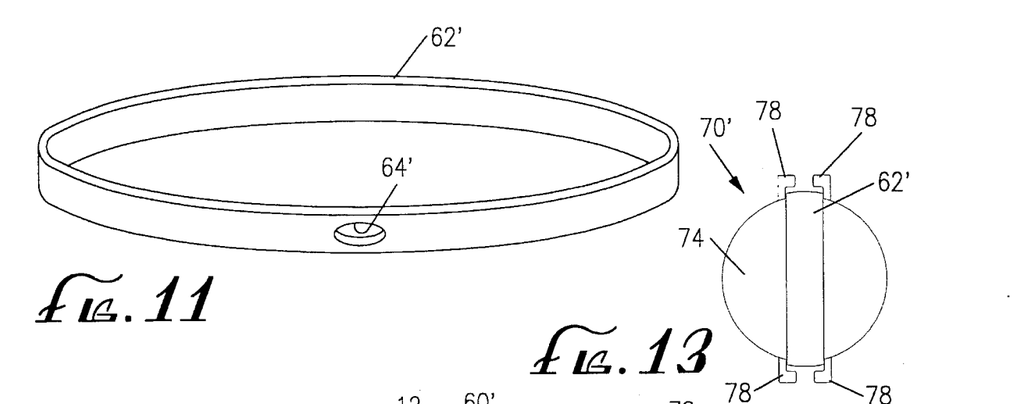
FIG. 11 is a perspective view of an elastic band configured for use in a modified form of the second preferred embodiment of the invention.
FIG. 13 is an elevational view, taken along line 13—13 of FIG. 12.
Figure 12:
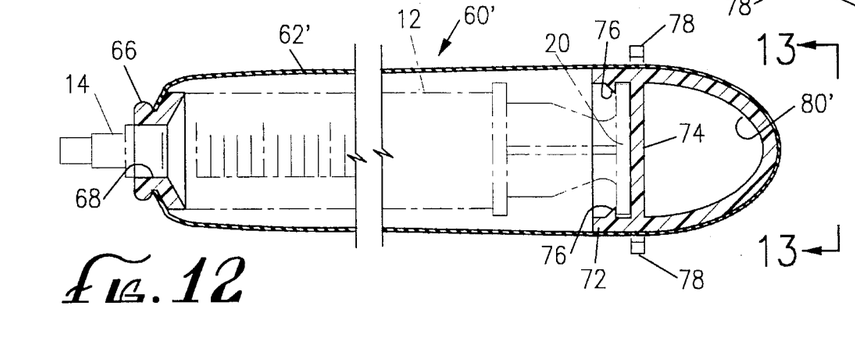
FIG. 12 is a cross-sectional view, similar to that of FIG. 9, showing the modified form of the second preferred embodiment of the invention installed on a syringe.
Figure 14:
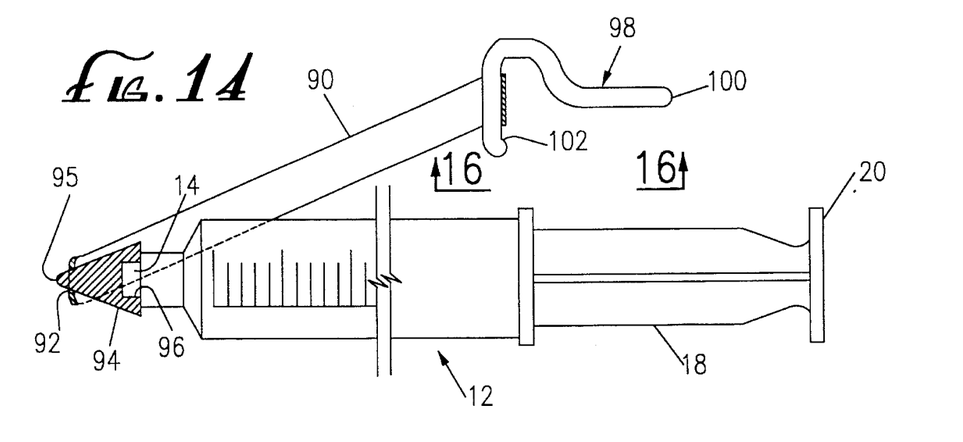
FIG. 14 is a side elevational view of a syringe, showing a third preferred embodiment of the invention, partially in cross-section, in the process of being installed on the syringe.

A modification of the second embodiment is illustrated in FIGS. 11, 12, and 13. In accordance with this modification, an elastomeric syringe actuation device 60' differs from the embodiment of FIGS. 8, 9, and 10 primarily in having an end cap 70' with a grip portion 80' that has a smooth, uninterrupted exterior surface, without any button or knob. Accordingly, in this modification, the device 60' employs an elastic band 62' that requires only a single hole 64' for the attachment of the band to the grommet 66, in the manner previously described. For being secured to the end cap 70', the band 62' relies on the guide fingers 78 and on frictional contact with the exterior surface of the grip portion 80'.

The second embodiment of FIGS. 8 through 13 is employed in a manner similar to that of the first embodiment of FIGS. 1 through 7. As compared to the first embodiment, the chief advantage of the second is lower cost, although it can accommodate a narrower range of syringe sizes.

A third preferred embodiment is shown in FIGS. 14–19. This embodiment comprises a continuous band or loop 90 of elastomeric material with a single hole 92; a tapered, preferably conical fitting 94, having a proximal apex 95, and a recess 96 in its base that removably receives the outlet tip 14 of the syringe 12; and a band-pulling implement 98.

Figure 16:
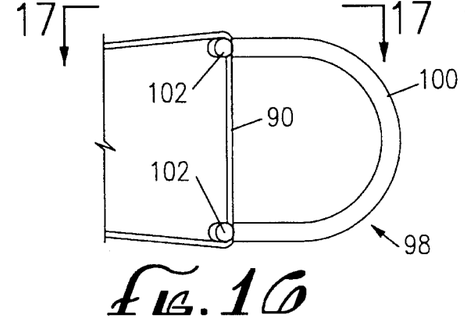
FIG. 16 is a plan view of the band-pulling implement of the embodiment of FIG. 14, taken along line 16—16 of FIG. 14.
Figure 17:
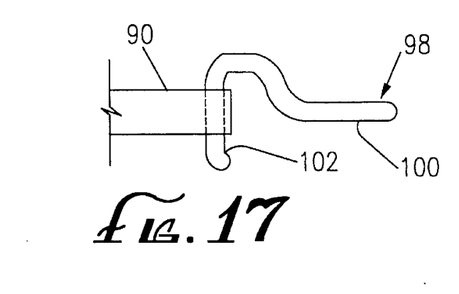
FIG. 17 is an elevational view of the band pulling implement of the FIG. 14 embodiment, taken along line 17—17 of FIG. 16.
Figure 18:
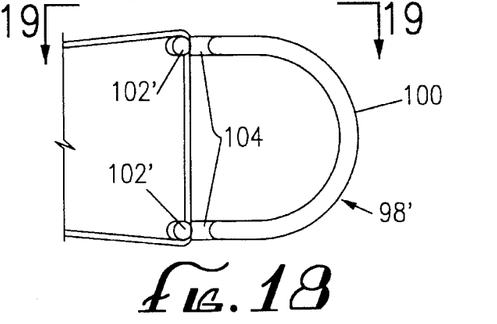
FIG. 18 is a plan view of a modified form of the band-pulling implement.
Figure 19:
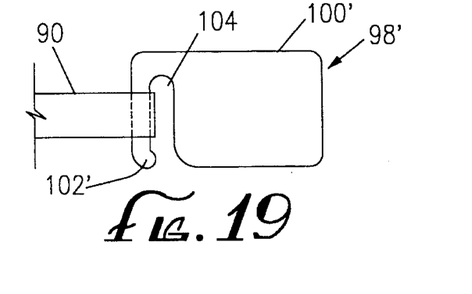
FIG. 19 is an elevational view of the band-pulling implement of FIG. 18, taken along line 19—19 of FIG. 18.

A preferred form of the band-pulling implement 98 is best shown in FIGS. 16 and 17. As shown, the band-pulling implement 98 comprises a handle portion 100, formed from a length of thick wire or tubular plastic, bent or molded in a U-shaped configuration, the opposed ends of which terminate in a pair of opposed, downwardly-depending hooking fingers 102. An alternative band-pulling implement 98', shown in FIGS. 18 and 19, comprises a handle portion 100' formed as an arcuate, U-shaped strip of plastic or metal, with a pair of downwardly-depending hooking fingers 102' defined by a pair of vertical slots 104 near the ends of the strip.

Figure 15:
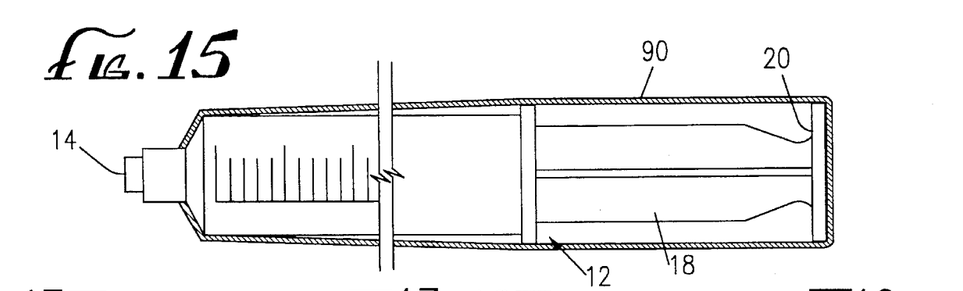
FIG. 15 is a view similar to that of FIG. 14, showing the elastic element fully installed on the syringe.

The third embodiment of the invention is used as follows: The conical fitting 94 is placed over the syringe outlet tip 14 by inserting the outlet tip 14 into the recess 96 in the base of the fitting 94. The elastomeric band 90 is installed on the proximal end of the syringe 12 by inserting the apex 95 of the fitting 94 into the hole 92 in the band 90. The band 90 is then engaged by the band-pulling implement 94 (94') by means of the hooking fingers 102 (102'), and the band is then pulled distally, using the implement 94 (94'), until the band is wrapped around and brought to bear against the thumb rest 20 of the syringe plunger 18, as shown in FIG. 15. When the syringe is to be used, the fitting 94 is removed, an IV administration set is attached, and the elastomeric band 90 is installed and actuates the plunger, as described above.

An advantage of the third embodiment is its simplicity of construction and use, as well as its ability to be used with a wide variety of conventional syringes. Furthermore, the fitting 94 maintains the sterility of the outlet tip 14, while also facilitating the installation of the elastomeric band 90.

FIGS. 20–32 illustrate a number of modifications and variations that may be employed in conjunction with one or more of the above-described embodiments.

Figure 24:
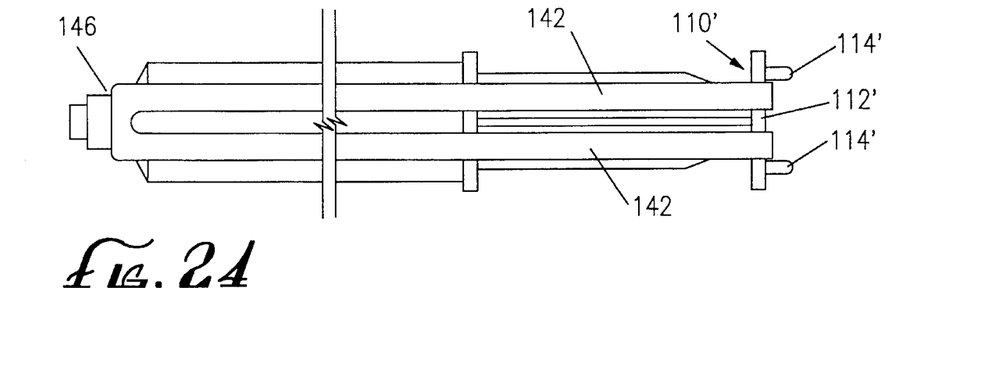
FIG. 24 is a plan view of the syringe of FIG. 23, showing the bifurcated elastomeric element fully installed.
Figure 25:
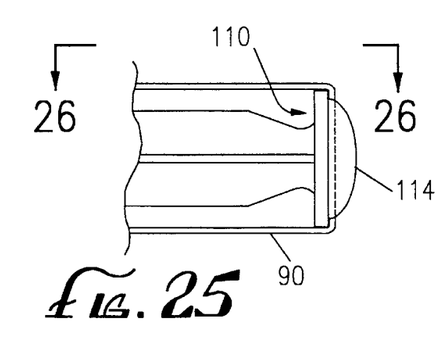
FIG. 25 is a partial elevational view of a modified plunger portion of the syringe of FIGS. 20, 21, 23, and 24.
Figures 26, 28:
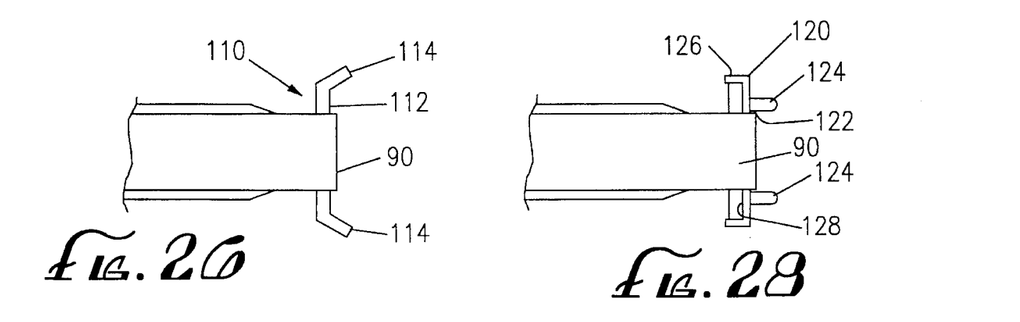
FIG. 26 is a plan view, taken along line 26—26 of FIG. 25.
FIG. 28 is a plan view, taken along line 28—28 of FIG. 27.

FIGS. 25–28, for example, illustrate modifications that may be advantageously employed with either the second or third embodiments, and especially the third embodiment. FIGS. 25 and 26 illustrate a modified plunger actuation portion 110 that may be incorporated into the plunger of a standard syringe. The modified actuation portion 110 comprises a flat distal end surface 112 defined between a pair of parallel, distally-extending flanges 114 that serve as guides for the elastomeric band 90, and keep the band from slipping off the actuation portion 110. The flanges or band guides 114 may flare radially outwardly from diametrically-opposed portions of the peripheral edge of the actuation portion 110, as shown in FIGS. 25 and 26. In an alternative form, shown in FIGS. 20, 21, 23, and 24, an actuation portion 110' has band guides or flanges 114' that are substantially perpendicular to a distal end surface 112', and that are spaced radially inwardly from the peripheral edge of the actuation portion 110'.

Figure 27:
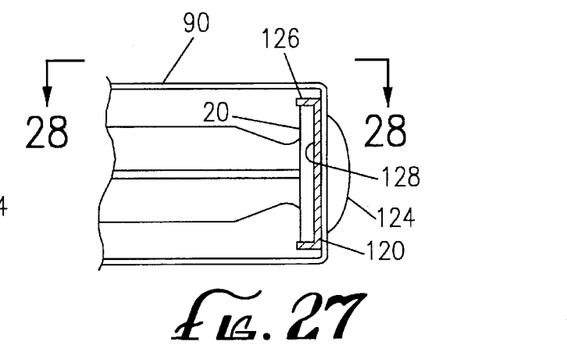
FIG. 27 is an elevational view of a modified end cap for use in the present invention.

FIGS. 27 and 28 illustrate a similar concept, embodied in a removable end cap 120 that fits over the standard plunger thumb rest 20. In this modification, a flat, band-receiving channel 122 is defined between pair of parallel band guides 124 that extend distally from the distal surface of the thumb rest 20. The band guides 124 may be perpendicular to the distal surface of the thumb rest 20, and spaced inwardly from the peripheral edge of the end cap 120. The band guides of the end cap may also have the flared configuration of FIG. 26. The end cap 120 also advantageously has a proximally-extending peripheral rim 126 that defines a proximal seating surface 128 for the thumb rest 20.

Figure 20:
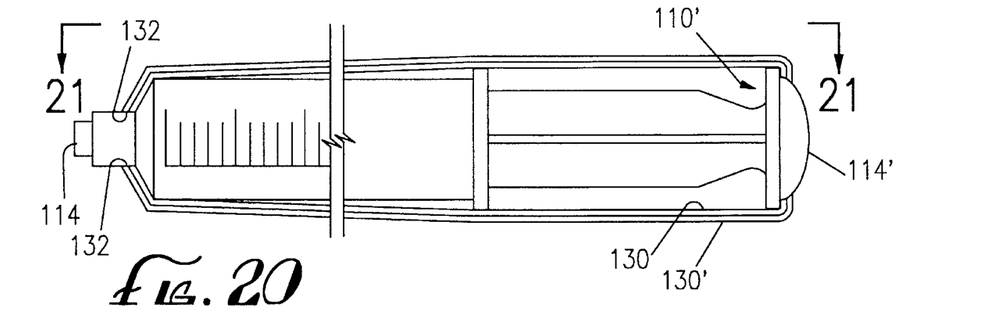
FIG. 20 is a side elevational view of a syringe, modified in accordance with a variation of the second preferred embodiment of the invention, and employing dual elastic bands.
Figure 21:
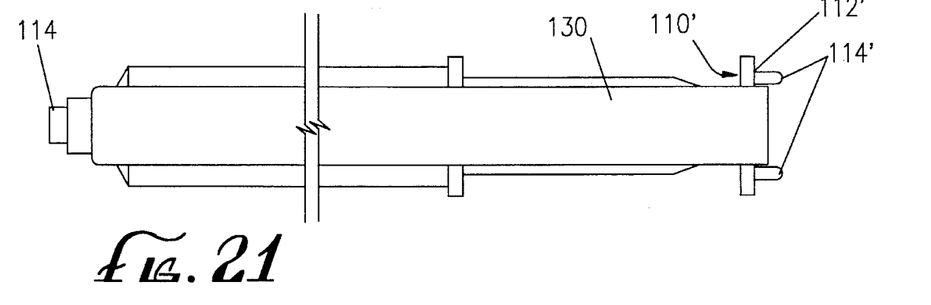
FIG. 21 is a plan view, taken along line 21—21 of FIG. 20.

FIGS. 20 and 21 illustrate another modification that may advantageously be used with the second and third embodiments of the invention. In this modification, at least two relatively weak elastomeric bands 130 are employed, rather than a single band. The two bands 130 are thinner than the single band that they would replace, so that each of them, individually, is easier to install. Specifically, each of the bands 130 has a hole 132, through which the outlet tip 14 of the syringe is inserted. Each of the bands is separately stretched distally over the actuation portion 110' of the plunger, thereby requiring less effort than the stretching of a single, relatively strong elastomeric band. This modification is thus suitable for use by individuals who may be weak or infirm.

Figure 22:
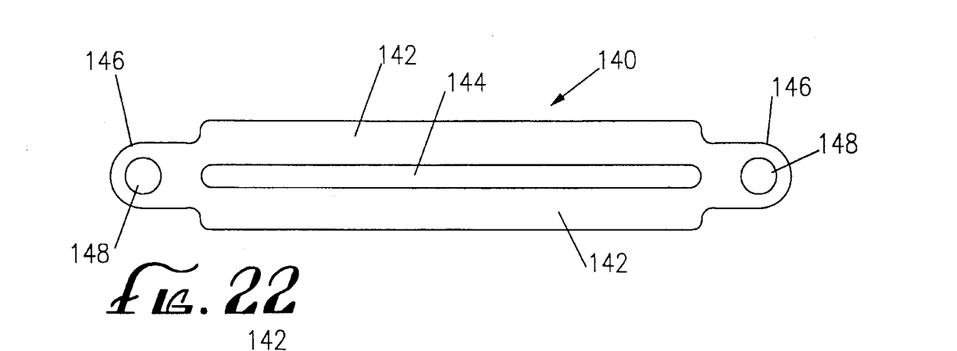
FIG. 22 is a plan view of a bifurcated elastomeric element that can be used in the present invention.
Figure 23:
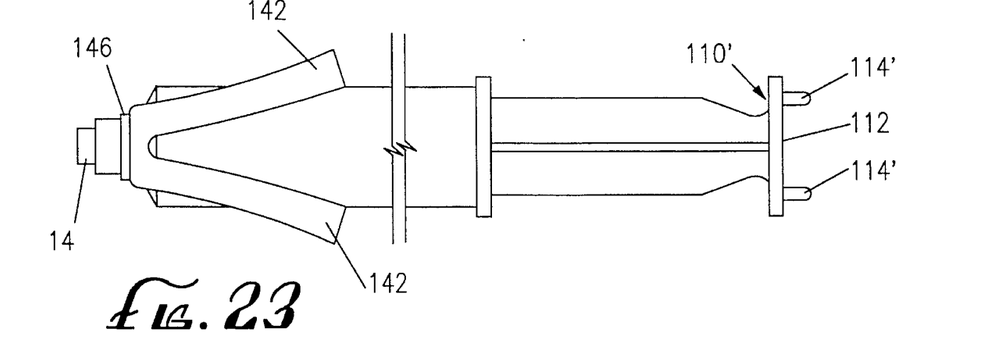
FIG. 23 is a plan view of a syringe, of the type shown in FIGS. 20 and 21, with the bifurcated elastomeric element of FIG. 22 in the process of being installed.

A similar concept is shown in FIGS. 22, 23, and 24. This modification employs a bifurcated elastomeric strap 140, best shown in FIG. 22, comprising a pair of parallel, relatively narrow strip elements 142 separated by a linear gap 144. The bifurcated strap 140 has a pair of opposed ends 146, at which the strip elements 144 are joined to each other. Each of the ends 146 has a hole 148.

The use of the bifurcated strap 140 is shown in FIGS. 23 and 24. First, the bifurcated strap 140 is folded over onto itself so that the ends 146 overlap with the holes 148 in alignment with each other. The strip elements 142 are spread so as to widen the gap 144 for the entry of the syringe between the strip elements 142, whereby the outlet tip 14 of the syringe is inserted through the aligned holes 148. Thus, as shown in FIG. 23, the two strip elements 142 are now disposed on diametrically opposite sides of the syringe barrel. Then, as shown in FIG. 24, each of the strip elements 142 is separately stretched distally over the thumb rest 110'. Thus, the bifurcated elastomeric strap 140 provides the above-described advantages of the dual band modification of FIGS. 20, and 21, but with the further convenience of using only a single elastomeric element, rather than two separate bands.

Figure 29:
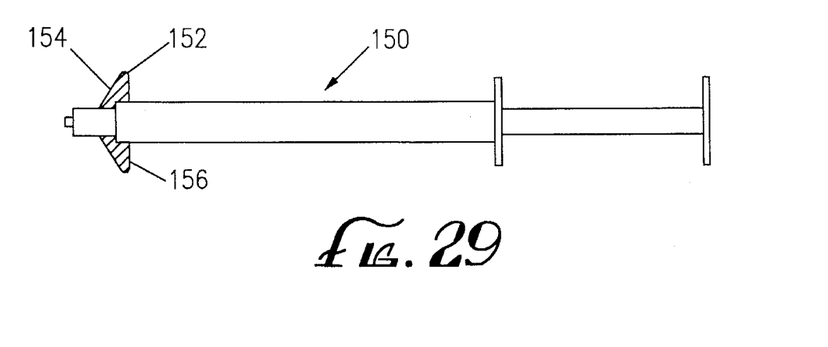
FIG. 29 is an elevational view, partly in cross section, showing a modification of a small diameter syringe to accommodate the present invention.

It is contemplated that the various embodiments and modifications of the present invention may be used with a wide variety of syringes, of various configurations and sizes. For small-diameter syringes, the outlet tip and the barrel may be of a diameter that is too small for proper engagement by the grommet assembly of the first and second embodiments. FIG. 29 illustrates how such a small-diameter syringe 150 may be modified for use with the present invention. In this modification, an annular bushing 152 is installed on the proximal end of the syringe 150 as an adapter that effectively increases the diameter of the syringe, so as to provide a bearing surface against which the grommet assembly can abut. The bushing 152 preferably has a substantially conical shape, with a tapered proximal surface 154 that facilitates installation of the grommet assembly, and a base 156 with a stepped orifice that receives and conforms to the exterior surface of the outlet tip and the proximal portion of the syringe barrel.

Figure 30:
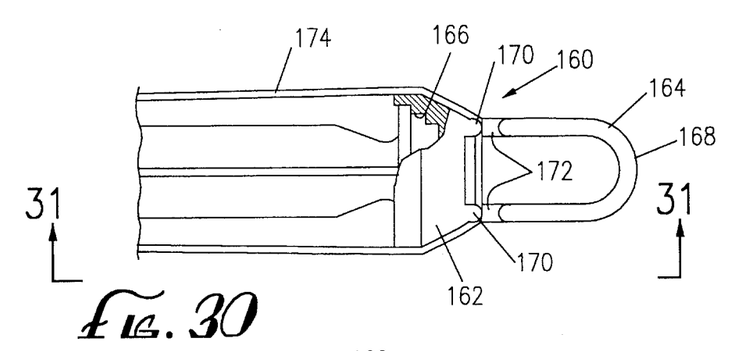
FIG. 30 is an elevational view, partially in cross section, of a modified end cap that can be used with the first and second preferred embodiments.
Figure 31:
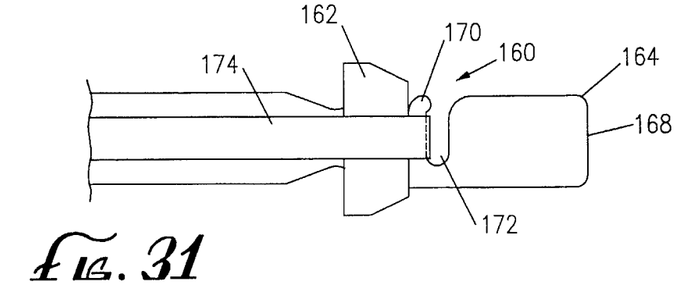
FIG. 31 is a plan view, taken along line 31—31 of FIG. 30.

FIGS. 30 and 31 illustrate still another modification that can be employed in any of the embodiments. This modification employs a combination end cap/band puller 160, comprising an end cap portion 162 having a distal end to which is attached a band puller portion 164. The end cap portion 162 and the band puller portion 164 are advantageously formed as a unitary component, such as a plastic molding.

The end cap portion 162 preferably has an interior 166 of stepped or graduated diameter, to accommodate syringe plunger thumb rests of different sizes. The band puller portion 164 preferably has the configuration of one of the band-pulling implements of the above-described third embodiment, as illustrated in FIGS. 14–19. As shown in FIGS. 30 and 31, the band puller portion is configured as the band-pulling implement 98' of FIGS. 18 and 19. Thus, it has a handle portion 168 formed as an arcuate, U-shaped strip of plastic or metal, with a pair of vertical hooking fingers 170, defined by a pair of vertical slots 172 near the ends of the strip. The combination end cap/band puller 160 can separated from a disposable elastomeric band 174, after use and then be re-used with a new band.

Figure 32:
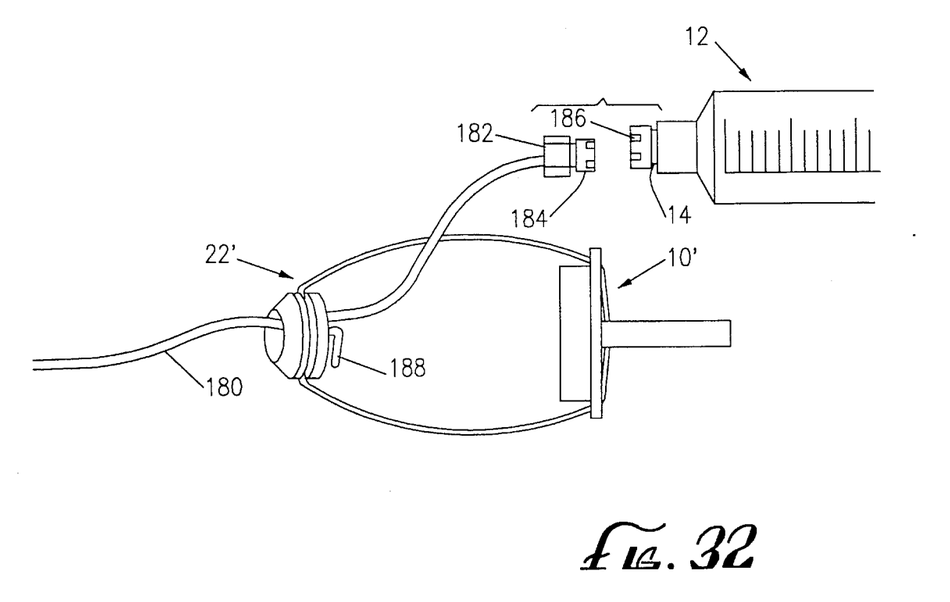
FIG. 32 is a plan view of a syringe and the first preferred embodiment of the invention, with the grommet assembly in perspective, showing a method of using the invention.

FIG. 32 illustrates how the present invention may be used in a manner that allows for the aseptic attachment of a sterile IV administration set to a sterile syringe 12. This method, illustrated with a syringe actuation device 10' that is similar to the above-described first embodiment, requires a grommet assembly 22' with a large enough internal diameter for the passage therethrough of an IV line 180 with a locking connector 182 and a closure cap 184. While the outlet tip 14 of the syringe is closed with a syringe cap 186, the capped end of the line 180 is passed through the grommet assembly 22', and a length of the line 180 is pulled through the grommet assembly 22'. The syringe cap 186 and the IV line closure cap 184 are removed, and the connector 182 is attached to the outlet tip 14 of the syringe. The procedure is simply reversed for the aseptic removal of the IV set from the syringe.

As shown in FIG. 32, the modified grommet assembly 22' includes an optional finger 188 for the attachment of the IV line 180 to the grommet assembly 22'.

From the foregoing description, it can be seen that the present invention provides an elastomerically-powered actuation device for an IV administration syringe that is easy and convenient to use, and that is adaptable to a wide variety of conventional IV administration syringes over a broad range of sizes. In addition, the present invention is simple and inexpensive to manufacture, and is therefore suitable for use as a disposable device. Furthermore, the invention provides a flow rate from the syringe that remains nearly constant until the syringe is substantially empty. Moreover, the present invention, in several embodiments, incorporates features that minimize the possibility of sudden separation of its components, either from each other or from the syringe, due to breakage of the elastomeric element.

Although the preferred embodiments of the invention and a number of modifications have been described herein, further variations and modifications may suggest themselves to those skilled in the pertinent arts. For example, the elastomeric actuation means might comprise a pair of elastic straps, each having one end fixed to a unitary grommet and the opposite end fixed to the end cap. Another variation might include a grommet assembly having two separable parts that snap together, rather than being threaded together. Other embodiments might include variations in the configuration of the finger grip and/or in the structure of the latching means in the end cap sleeve. These and other variations and modifications that may suggest themselves are considered to be within the spirit and scope of the present invention, as defined in the claims that follow.

What is claimed is:

1. A device for actuating a syringe having a barrel for containing a supply of fluid, the barrel having a proximal end terminating in an outlet tip, and a plunger slidably disposed within the barrel for movement between a withdrawn position and an inserted position, the plunger having an actuation portion extending distally from the barrel, the device comprising:

a continuous elastomeric band having outlet tip engagement means for removably attaching the band to the outlet tip; and band-pulling means, removably engageable with the band when the band is removably attached to the outlet tip, for allowing the band to be pulled distally so as to seat against the actuation portion, the band-pulling means comprising:

a band-engaging portion that includes a generally U-shaped member having a pair of opposed ends; and a handle portion, attached to the band-engaging portion, that includes a finger projecting from each of the opposed ends.

2. The device of claim 1, wherein the outlet tip engagement means includes a hole in the band that is dimensioned to receive the outlet tip.

3. The device of claim 1, wherein the U-shaped member is a flattened strip having a pair of opposed ends; and wherein each of the fingers is defined by a slot in the strip near each of the opposed ends.

4. The device of claim 1, wherein the band-pulling means further comprises:

plunger engagement means for engaging the actuation portion of the plunger, the plunger engagement means including a distal end to which the band-pulling means is attached.

5. The device of claim 4, wherein the plunger engagement means includes an end cap having a graduated internal diameter.

6. The device of claims 1, 2, 3, 4, or 5, wherein the outlet tip engagement means includes a tapered fitting, removably attachable to the outlet tip, and dimensioned to be inserted through the hole in the band.

7. The device of claim 6, further comprising first and second continuous elastomeric bands, wherein the band-pulling means are removably engageable with the first and second bands, for allowing the first and second bands to be individually pulled distally, so as to seat against the actuation portion.

8. The device of claims 1, 2, 3, 4, or 5, further comprising first and second continuous elastomeric bands, wherein the band-pulling means are removably engageable with the first and second bands, for allowing the first and second bands to be individually pulled distally, so as to seat against the actuation portion.

9. A device for actuating a syringe having a barrel for containing a supply of fluid, the barrel having a proximal end terminating in an outlet tip, and a plunger slidably disposed within the barrel for movement between a withdrawn position and an inserted position, the plunger having an actuation portion extending distally from the barrel, the device comprising:

a bifurcated elastomeric strap, comprising a pair of parallel strip elements separated by a linear gap, the strap having first and second ends at which the strip elements are conjoined, each of the first and second ends having a hole dimensioned to receive the outlet tip;

whereby the strap is foldable over onto itself so as to align the holes in the first and second ends with each other so as to allow the outlet tip to be inserted therethrough, and so as to allow the strip elements to be individually pulled distally so as to seat against the actuation portion.

10. The device of claim 9, further comprising an end cap that is removably engageable with the actuation portion.

11. The device of claim 10, wherein the end cap has a distal surface defined between a pair of substantially parallel, substantially distally-extending band guide elements.

12. The device of claim 11, wherein the end cap has a peripheral edge, and wherein the band guide elements flare radially outwardly from diametrically-opposed portions of the peripheral edge.

13. The device of claim 11, wherein the end cap has a peripheral edge, and wherein the band guide elements are substantially perpendicular to the distal surface and are spaced radially inwardly from the peripheral edge.

14. An improved syringe, of the type having a barrel for containing a supply of fluid, the barrel having a proximal end terminating in an outlet tip, and a plunger slidably disposed within the barrel for movement between a withdrawn position and an inserted position, the plunger having an actuation portion extending distally from the barrel, the improvement comprising:

band guide means on the actuation portion; and an elastomeric element removably attachable to the outlet tip, and stretchable distally so as to seat against the actuation portion between the band guide means, the elastomeric element comprising a bifurcated elastomeric strap, comprising a pair of parallel strip elements separated by a linear gap, the strap having first and second ends at which the strip elements are conjoined, each of the first and second ends having a hole dimensioned to receive the outlet tip;

whereby the strap is foldable over onto itself so as to align the holes in the first and second ends with each other so as to allow the outlet tip to be inserted therethrough, and so as to allow the strip elements to be individually pulled distally so as to seat against the actuation portion.

15. The improvement of claim 14, wherein the band guide means are integral with the actuation portion.

16. The improvement of claim 15, wherein the actuation portion includes a substantially flat distal surface, and wherein the band guide means comprise a pair of substantially parallel band guide elements, extending substantially distally from the distal surface.

17. The improvement of claim 16, wherein the actuation portion has a peripheral edge, and wherein the band guide elements flare radially outwardly from diametrically-opposed portions of the peripheral edge.

18. The improvement of claim 16, wherein the actuation portion has a peripheral edge, and wherein the band guide elements are substantially perpendicular to the distal surface and are spaced radially inwardly from the peripheral edge.

19. The improvement of claim 14, further comprising an end cap that is removably engageable with the actuation portion, wherein the band guide means are on the end cap.

20. The improvement of claim 19, wherein the end cap includes a substantially flat distal surface, and wherein the band guide means comprise a pair of substantially parallel band guide elements, extending substantially distally from the distal surface.

21. The improvement of claim 20, wherein the end cap has a peripheral edge, and wherein the band guide elements flare radially outwardly from diametrically-opposed portions of the peripheral edge.

22. The improvement of claim 20, wherein the end cap has a peripheral edge, and wherein the band guide elements are substantially perpendicular to the distal surface and are spaced radially inwardly from the peripheral edge.

* * * * *